United States Patent [19]

Lee

[11] Patent Number: 4,730,623
[45] Date of Patent: Mar. 15, 1988

[54] CARDIAC OUTPUT ESTIMATION METHOD AND APPARATUS

[76] Inventor: Arnold St. J. Lee, 1033 Hilts Ave., Los Angeles, Calif. 90024

[21] Appl. No.: 744,757

[22] Filed: Jun. 14, 1985

[51] Int. Cl.$^4$ .................................................. A61B 5/02
[52] U.S. Cl. ..................................... 128/692; 128/736; 73/204
[58] Field of Search ............................... 128/691–692, 128/736, 670; 73/204

[56] References Cited

U.S. PATENT DOCUMENTS

| | | | |
|---|---|---|---|
| 3,561,266 | 2/1971 | Auphan et al. | 128/692 X |
| 4,016,759 | 4/1977 | Baker et al. | 73/204 |
| 4,191,194 | 3/1980 | Watanabe et al. | 128/692 |
| 4,217,910 | 8/1980 | Khalil | 128/692 X |
| 4,240,441 | 12/1980 | Khalil | 128/692 |
| 4,502,488 | 3/1985 | Degironimo et al. | 128/692 |
| 4,576,182 | 3/1986 | Normann | 128/692 |
| 4,599,895 | 7/1986 | Wiseman | 73/204 |

FOREIGN PATENT DOCUMENTS 0923520 4/1982 U.S.S.R. ............... 128/692

OTHER PUBLICATIONS

Johnson et al., "A Spher. Heated Thermocouple Probe For Perfusion Measurements"; *Conf.; 1978 Advances in Bioengr.*, 12-1978, pp. 159–162.

Primary Examiner—Edward M. Coven
Assistant Examiner—Angela D. Sykes
Attorney, Agent, or Firm—Spensley Horn Jubas & Lubitz

[57] ABSTRACT

Thermocouple pairs measure the temperatures at a cold-fluid injection point and a downstream point. The reference thermocouple of each pair sees the temperature of a thermally floating heat sink of unknown temperature that has high thermal conductivity and mass, and is well insulated from the environment. Consequently the heat-sink temperature drift is practically constant. To the extent that heat-sink temperature drift is significant, the invention overcomes the effects of drift to a first approximation by providing electronic circuitry that in effect registers the drift in measurement voltage before fluid injection, extrapolates this voltage drift into the measurement time period, and automatically subtracts the extrapolated voltage drift from the measurement voltages.

14 Claims, 7 Drawing Figures

CARDIAC OUTPUT ESTIMATION METHOD AND APPARATUS

BACKGROUND

1. Field of the Invention

This invention relates generally to methods and apparatus for estimating the flow rate of blood from the heart, and more particularly to an improved "thermal dilution method" of making estimates and improved apparatus for use in that method.

2. Prior Art

A currently usual technique, called the "thermal dilution method," for estimating the rate of flow of blood from a living patient's heart is to inject a bolus of cold fluid, which in this document will be called "injectate," into the entrance of the heart, and to record the temperature of the thoroughly mixed blood downstream from the heart. The temperature recording proceeds as a function of time, and over an interval necessary to estimate the mean temperature change—normally less than twenty seconds.

The average temperature of the injectate is estimated by measurement at the point of entry into the catheter, or by actually measuring the temperature of the injectate "bath," in which the injectate syringe is cooled, or by forcing the injectate to asssume the temperature of melting ice by long "soaking" in a mixture of water and ice.

The temperature sensors most commonly used for the required blood-temperature measurements have been thermistors, since they have a high sensitivity—on the order of 10,000 microvolts per degree Celsius. Precise precalibrated thermistors, however, are expensive, since they are employed in single-use (or disposable) equipment.

Thermocouples have not been as widely used, for two reasons. First, their output is much lower—on the order of fifty microvolts per degree. Second, they have been used with costly and inconvenient thermostatted reference-temperature devices, which will be discussed further below.

Thermocouples have the advantage of low cost, since they consist of a pair of wires that can be cheaply purchased in very large quantities from a single "melt" batch of identical Seebeck-coefficient alloy. Furthermore, since the output voltage calibration of thermocouples depends solely upon the materials of their wires, only sporadic calibration is necessary in the manufacturing process.

In view of these unrealized advantages, it is worthwhile to explore the previously mentioned disadvantages of thermocouples in greater detail, to understand their causes, ramifications, and possible mitigations.

First, the low voltage output of thermocouples requires high amplification to provide usable signals. High amplification in turn has been associated with either poor stability, and/or frequent adjustment.

Second, the reference-temperature device—which in this document will be called the "reference heat sink" is necessary because of the well-known requirement for using thermocouples in pairs. A thermocouple consists of two wires of dissimilar material joined at a "junction" and respectively extending away from the junction. Two identical thermocouples connected together at one point by their similar-metal wires, form a "thermocouple pair." One junction of the pair is designated the "sensing" junction and the other the "reference" junction.

The voltage output of such a thermocouple pair is the open-circuit voltage measurable between the nonjoined similar-metal wires of the thermocouple pair. This voltage is approximately proportional to the temperature *difference* between the sensing and reference junctions, especially in a narrow temperature range of interest in this field. Consequently the sensing junction is placed in a location where the temperature is to be sensed, and the reference junction conventionally is placed in a reference heat sink of precisely known temperature. The temperature to be measured is then found as the difference between (1) the voltage output of the pair, multiplied by the calibration factor in degrees per volt, and (2) the known reference temperature of the reference heat sink.

It is common to use for the reference heat sink an insulated container filled with pure ice and pure water, so that the reference junction is maintained at exactly zero degrees Celsius.

It is inconvenient to use pure ice and water. Moreover, there is a large temperature difference between the junctions—for example, 37 Celsius degrees between blood in the human body and the freezing point of water. Therefore the change in thermocouple voltage output for small temperature deviations is very small compared to the total voltage across the thermocouples. As is well known, such a relationship adds to measurement inaccuracy.

For example, where the blood is at 37 degrees Celsius, the output from a thermocouple pair referred to icewater is approximately 1,480 microvolts. A typical peak change in blood temperature when injectate is introduced is $-0.5$ degree Celsius, leading to a change in thermocouple-pair output of only about twenty microvolts. Thus the change in output would be only about 20/1480 or 1.5 percent of the total output at the peak, and perhaps 0.3 percent at the mean temperature.

Alternatively, commercial circuit elements are available which provide "temperature-compensation" voltage outputs that may be substituted for the output of the reference junction in the reference heat sink. These elements are inexact, demonstrating drift and noise deleterious to extremely accurate measurements, while adding substantially to the cost of the electronics.

SUMMARY OF THE INVENTION

My invention provides method and apparatus that use thermocouples to measure both the changing blood temperature as a result of the injectate administration, and preferably also the mean injectate temperature at the site of its entry into the bloodstream—in a mode which compensates for all first-order sources of error. These measurements are economical and extremely accurate because the system is (1) "zeroed" automatically just before injectate adjmission, thus being affected by only about twenty seconds of drift during the measurement interval, and (2) automatically compensated for much of the constant portion of any such drift.

The system includes a special kind of reference heat sink coupled to the reference junction. This reference heat sink need not be maintained at a controlled temperature; however, the heat sink material is of high thermal conductivity, and the heat sink has considerable mass and it is thermally insulated from the environment so that its temperature (whether or not known) remains constant to a first approximation throughout the measurement procedure.

In many practical applications it is desirable to determine on an absolute (but approximate) basis the temperature of the reference heat sink or of the patient's body—for purposes other than cardiac flow-rate measurement. Hence it cannot be said categorically that in my invention neither the reference heat-sink temperature nor the patient's body temperature is known. It is categorically true, however, that in the cardiac flow-rate measurement apparatus or method of my invention neither of these temperature values, considered singly, is used.

My invention works independently of the temperature of the heat sink considered singly. It also works independently of the temperature of the patient's body considered singly. Rather it is responsive only to the differential output from two thermocouples operating as an opposed thermocouple pair.

Furthermore, even if it is known, the heat-sink or body temperature is usually not known to the very high precision required of difference measurements in determining cardiac flow according to my invention.

In the apparatus of my invention an offset voltage is added into the thermocouple amplifier to bring its output to zero, and this offset voltage is maintained constant during the measurement procedure.

Thus, while the initial temperature of the blood is not necessarily measured on an absolute basis—that is, with respect to any known temperature—any change in temperature can be measured very precisely.

The heat sink can be a suitable mass of any material of high thermal conductivity, such as copper. The heat sink need have no temperature-control apparatus, and thus may simply "float" thermally at a temperature representing a mean of its environment's temperature history.

In some embodiments of my invention it may be desirable, e.g., for purposes of miniaturization, to reduce the volume and mass of the heat sink. As volume and mass are reduced, the ratio of external area (and therefore of heat loss through the insulation) to mass increases. As such miniaturization continues a point will be reached at which the temperature difference between the heat sink and ambient causes a nonnegligible rate of heat-sink temperature drift during the measurement. In addition, amplifying and other analog circuits always exhibit some drift, often not negligible.

My invention accordingly provides electronic circuitry that compensates for the constant portion of such nonnegligible drift, and thereby permits precise recording of the small temperature deviations of the bloodstream with a miniaturized reference heat sink despite such drift.

All of the foregoing operational principles and advantages of the invention will be more fully appreciated upon consideration of the following detailed description, with reference to the appended drawings, of which:

BRIEF DESCRIPTION OF THE DRAWINGS

FIG. 7 is a sectional view taken along line A—A' of FIG. 1.

DETAILED DESCRIPTION OF THE PREFERRED EMBODIMENTS

Figure 1:
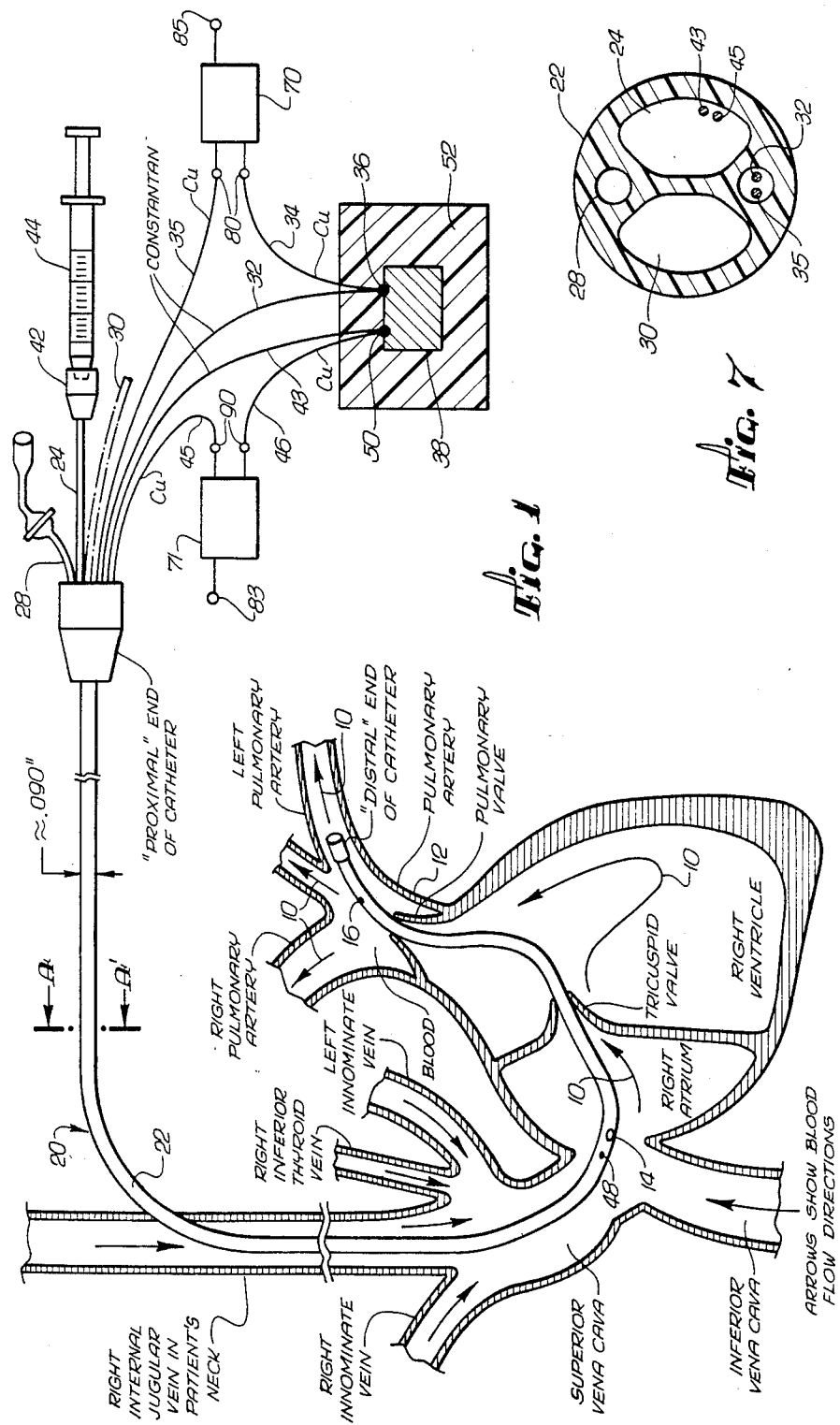
FIG. 1 is a highly schematic diagram of a preferred embodiment of apparatus in accordance with my invention, shown emplaced within a living human patient's body.

The system shown in FIG. 1 can be used to measure the rate of flow of blood 10 in a blood vessel 12. The system includes a commercial blood-flow measuring apparatus 20, called a "flow-directed thermal-dilution cardiac catheter," with substitution of a thermocouple for the usual thermistor, and with the addition of a second thermocouple for measuring injectate temperature at the point of entry into the bloodstream.

The technique for using this system to measure flow rate includes injection, as at 14, of a bolus of relatively cool liquid into the blood. The technique also includes measurement of the resulting instantaneous change in temperature of the blood at a point 16 that is sufficiently far downstream from the injection point 14 to ensure thorough intervening mixing but not so far as to allow significant heat loss, for a sufficient time interval to enable calculation of the mean bloodstream temperature drop caused by the injection. The injectate is introduced into the blood rapidly, and the amount and temperature of the injectate are known; consequently measuring changes in temperature in the blood at the downstream location 16 enables an accurate estimation of the flow rate of blood in the vessel.

The apparatus 20 includes a catheter 22, and this catheter has a lumen or internal conduit 24 that can carry injectate. The catheter 22 also has a thermocouple with a sensing junction at 16, used to measure changes in blood temperature. The catheter 22 is generally of a type that includes the additional tubes 28, 30 used for purposes not directly related to the present invention.

A reference thermocouple 36 includes the welded connection of two wires 32, 34, at their ends. These wires are of dissimilar materials, e.g., constantan and copper. The constantan wire is welded at its opposite end to a second constantan wire—whose other end is welded to a second copper wire 35 to form the sensing junction at 16. The second copper wire 35 leaves the proximal end of the apparatus 20, along with copper wire 34 to be attached to the input of the voltage-measuring circuit 70. The reference thermocouple 36 is disposed within a heat sink 38 of a material which maintains a relatively constant (though possibly unknown) temperature throughout the measurement procedure, which lasts about twenty seconds. The combined effect of the heat-sink mass and insulation provides a long time constant, so that any drift in heat-sink temperature during the interval is essentially constant.

The system also includes a syringe receiver 42, which has an outlet connected to the tube 24 that carries injectate into the blood vessel, and an inlet that can be connected to a syringe 44. The syringe is used to hold injectate, and at the proper time to inject it into the tube 24. Upon injection the injectate passes out through the opening at 14 in the catheter, to flow into the blood vessel or heart entrance.

Also provided is another thermocouple pair, which includes a sensing junction 48 in the injectate tube near the outlet 14 in the cathether. This thermocouple pair also includes a second reference junction at 50, connected by a constantan wire 43, in the previously mentioned heat sink. This second thermocouple pair enables determination (or estimation) of the mean temperature (over volume) of the injectate at the point where it is injected into the bloodstream, provided that a signal representing instantaneous injected volume is available.

The relevant measurement by this second sensing junction 48 is the difference between the mean injectate temperature at 14 and the initial blood temperature sensed at 16 before addition of the injectate. The quantity of injectate is determined using the markings on the syringe.

It is important to note that neither of the reference junctions and neither of the sensing junctions is connected in such a way as to permit measurement of any of the temperatures on an absolute basis—i.e., referred to any known temperature. Although the patient's body temperature or the reference heat-sink temperature may be known from other measurements or for other purposes, no such temperature value is used in either the apparatus or the method of my invention—and as previously mentioned such a temperature value is not usually known to the level of precision that is essential in making difference measurements for cardiac-flow determinations.

The apparatus and method of my invention are completely independent of the temperature of the reference heat sink considered singly, and completely independent of the temperature of the patient's body considered singly.

A digital computer (or an analog data processor) can be programmed to receive information as to the quantity of injectate, the differential injectate temperature referred to the initial or "original" blood temperature at equally-spaced volume quanta, and the corresponding decrease in temperature at 48 of the blood at the location 16, at equally spaced time intervals. The computer can also be programmed to use these basic data to calculate the rate of flow of blood through the blood vessel 12.

As previously mentioned, my reference heat sink is preferably of copper or like highly heat-conductive material, which by ready internal conduction within the heat-sink block assures that the temperature is substantially the same in all regions of the block of material. Therefore, even if there is a slight heating or cooling of the block at its surface, the effect of such heat gain or loss is averaged over the entire mass of the block, and will result in minimal temperature change at the measurement point.

Insulation 52 is used to isolate the heat sink from the environment, to minimize its temperature change during the measurement interval, and, therefore, to cause that rate to remain essentially constant (albeit very small) during the measurement interval.

Figure 2:
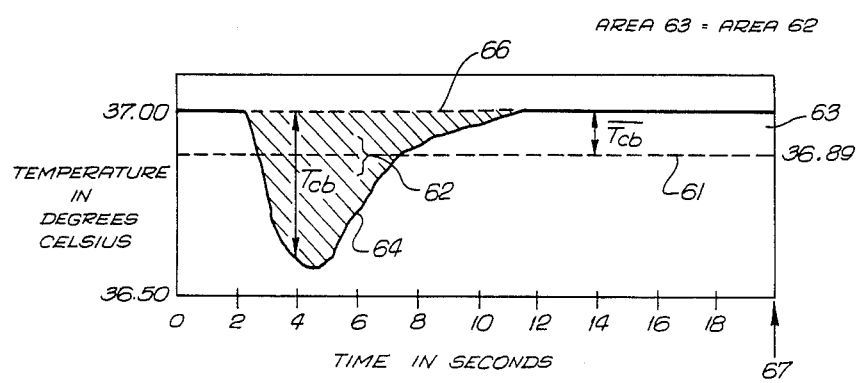
FIG. 2 is a graph showing the change in blood temperature during a selected measurement procedure, performed with the apparatus of FIG. 1.

As shown in FIG. 2, in response to the injection of cold fluid the blood temperature may drop by a peak termperature between 0.5 and 5.0 degrees Celsius between the time prior to the injection of the cold fluid and the time immediately following the injection, which in this document is called the "measurement interval." The blood will have returned to its original (preinjection) temperature in about twenty seconds within an accuracy suitable to this procedure. These are typical figures for flow rates between 1,000 and 10,000 cubic centimeters per minute; and for five to ten cubic centimeters of injectate at zero to twenty-five degrees Celsius, introduced into the right auricle over a period of two to three seconds.

It is possible to estimate the flow rate of blood by measuring the instantaneous temperature drop over time. If, however, the injectate temperature at 14 is not measured and integrated as a function of injected volume, the calculated flow rate will depend somewhat upon the injection rate—because of the variable heating of the injectate before exit at 14. Greater accuracy therefore can be obtained by determining the required injectate mean temperature on the basis of the volume integral of the injectate temperature difference from the "original" blood temperature.

Figure 3:
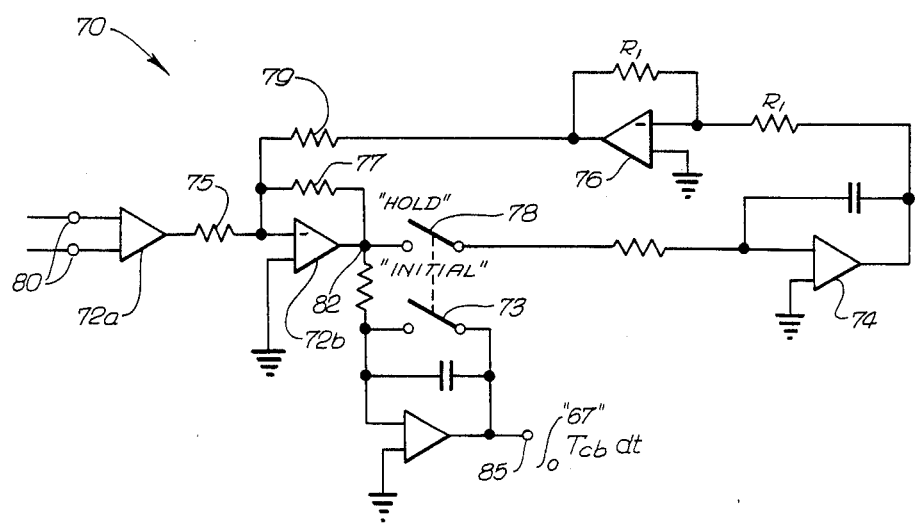
FIG. 3 is a schematic diagram of a circuit for use in the FIG. 1 embodiment.

For computing the area between curve 64 and line 66, a necessary prelude to determining the mean change in blood temperature caused by the injection, the circuit 70—whose details appear in FIG. 3—provides a simplified means for generating a signal representing the integral of temperature change versus time.

The combination of a differential-gain preamplifier 72a followed by the operational amplifier ("op amp") 72b—which are usually contained in a single "instrumentation amplifier" package—also forms part of a zeroing circuit which includes a switch 78. The voltage developed by the thermocouple 16 represents a measurement of the temperature of the blood in series opposition with thermocouple 36 in the reference heat sink. This measurement voltage is delivered at inputs 80 of the preamplifier 72a, is amplified and delivered to the summing junction of the inverting "adder" consisting of op amp 72b together with resistors 75 and 77.

With switch 78 closed, the integrator including amplifier 74 adds a "balancing" signal into the summing junction of the op amp 72b, in such polarity as to cause the voltage at 82 to go to zero. The amplifier 76 with resistors R1 causes the required inversion.

Immediately before injectate is introduced into the blood, the switch 78 is opened, causing the balancing signal to be held—i. e., the preinjection temperature is in effect "remembered." Upon introduction of the injectate, the voltage across the input terminals 80 will drop and then rise again in a pattern similar to that shown in FIG. 2. The voltage at 82, however, being balanced at zero immediately before the injection, will assume the pattern 64 in FIG. 2, so that the integrator including op amp 71 will present at 85 an output voltage at the end of the measuring cycle 67 proportional to the area 62.

The rate of flow of blood is substantially inversely related to the voltage at the output 85 of the circuit. The time interval during which the injection occurs, as the procedure is currently practiced in hospitals—e.g., between one-half second and five seconds—does affect the voltage output on line 85, because the injectate temperature increases by an unknown amount during its transit to the point 14. Thus estimating or measuring the injectate temperature before injection at point 14 leads to significant error.

To avoid or compensate for such error, the injectate temperature is measured at 14, and that temperature is integrated over injected volume, rather than time. The result of this calculation is the true mean injectate temperature, and the resultant flow-rate calculation may be rendered independent of injection rate—except that if the injection is unduly prolonged the point in time when the blood temperture returns to preinjection temperature will be difficult to determine.

The actual relationship between the determined flow rate Q, the mean temperature change $T_b$ bloodstream caused by the injectate, the mean temperature difference $T_i$ of the injectate from the initial blood temperature, the injectate volume V and the measurement period P is approximately: $Q=1.08\times(V/P)\times(T_i/T_b-1)$, if the injectate is normal saline solution. In practice the unity term is substantially smaller than the ratio $T_i/T_b$, and is therefore customarily neglected by workers in the field. It will be understood that this relationship is presented here only for reference, and is thoroughly developed and discussed in the literature.

If for purposes of miniaturization the mass of the reference heat sink is reduced considerably, there will develop a significant rate of change of temperature of the heat sink during the measurement period. A component of this rate of change—and of the drifts in most amplifiers and other circuit elements—may be regarded as constant. The circuit of FIG. 4 will compensate for such a substantially constant component of drift.

Figure 4:
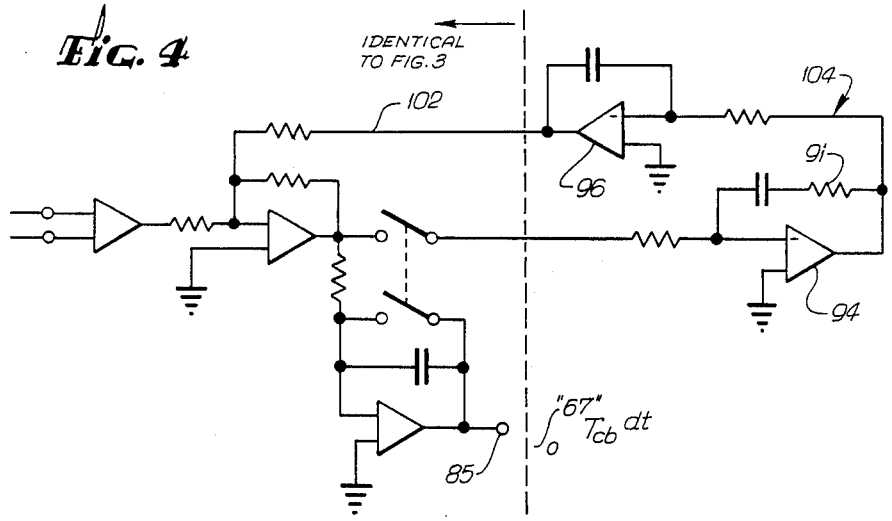
FIG. 4 is a similar diagram of a preferred circuit for use in the FIG. 1 embodiment.

In FIG. 4 everything to the left of the dashed line is identical in form and function to FIG. 3. The integrator of FIG. 3, including op amp 74, is modified by the addition of resistor 91. The inverter of FIG. 3, including the op amp 76, is changed to the integrator, including op amp 96, of FIG. 4.

As in the previous functional explanation of FIG. 3, this circuit, with switch 78 closed, will balance out any input voltage at 80, forcing the voltage on 82 to zero. If, however, there is a constant rate of change of the voltage at 82, the feedback voltage (i.e., the balancing signal at 102) required to balance out the constant voltage drift at 82 also has a constant rate of change. If the output of an integrator is forced to change at a constant rate, the input to that integrator, as on line 104, is constrained to be a constant voltage.

Thus, when the switch 78 is opened and the output of the op amp 94 on line 104 is held constant, the balancing signal at 102 will continue its previous rate of change, thus continuing the balance in the face of a continuing constant rate of temperature change of the reference heat sink.

When the circuit of FIG. 3, which is unconditionally stable, is changed to that of FIG. 4, an oscillation around the balance may develop. This instability is controlled by the addition of a damping resistor 91 in series with the integrating capacitor of the op amp 94. The resistor 91, greater than 1,000 ohms (for a two-microfarad capacitor), stabilizes the integrator without significantly affecting the accuracy of the circuit. The integrator has a one-second time constant.

Figure 5:
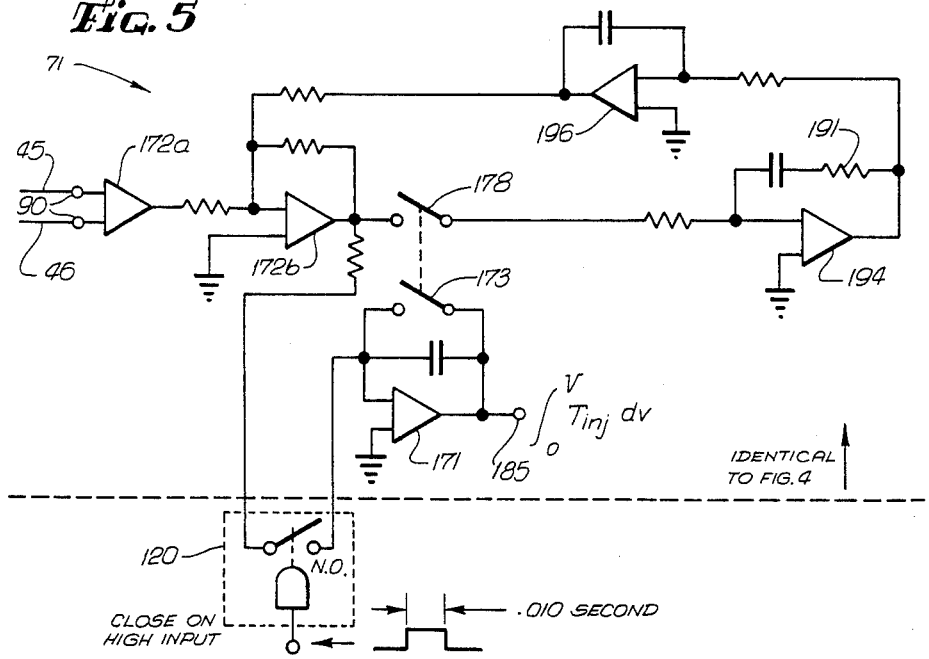
FIG. 5 is a schematic diagram of another preferred circuit for use in the FIG. 1 embodiment; this particular circuit calculates the volume integral of the injectate temperature difference from the "original" blood temperature, to provide the true mean injectate temperature.
Figure 6:
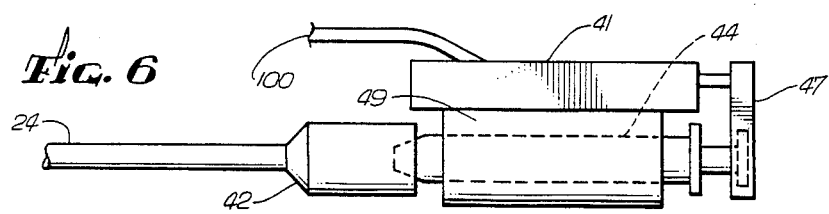
FIG. 6 shows an injected-volume transducer connected to the injectate syringe, which produces an output pulse as each equal predetermined quantum of injectate is added.

FIG. 5 shows a circuit for obtaining the integral of the injectate temperature, referred to the initial blood temperature, over volume. When this integral is divided by the injectate total volume, the quotient is the mean effective injectate temperature. By way of reiteration, whereas FIG. 4 provides at its output 85 the integral of a measured temperature deviation from a previous initial temperature over time, FIG. 5 provides at its output 185 an analogous integral over volume. The latter circuit works as follows.

A switch 120, preferably electronic, is interposed between the gain amplifier including the op amp 172b output and the input to the integrator including the op amp 171. The switch 120 conducts for a predetermined constant time, say ten milliseconds, at each closure.

The volume transducer 41, attached to the syringe 44 by clamps 49 and 47, emits on its output wires 100 a pulse as each tenth of a cubic centimeter of injectate leaves the syringe. Each of these pulses triggers the switch 120, causing the voltage at 182 (which represents the temperature of the injectate relative to the initial blood temperature) to be applied to the integrator that includes the op amp 171. This application continues for ten milliseconds, causing the op-amp output at 185 to "jump up" a voltage step proportional to the effective temperature of that volume quantum. When the injection is complete, a voltage will stand at 185 (FIG. 5) that is proportional to the mean effective injectate temperature.

In this way the invention provides an improvement in the apparatus as well as the method for measuring blood flow by thermal dilution. The invention facilitates the use of much less expensive thermocouples with extreme accuracy, by providing a reference heat sink that is easy to use and yet highly accurate.

Use of my invention is optimized by ensuring that the nonlinear component of reference-heat-sink temperature drift is negligible. This can be accomplished by allowing the heat sink to closely approach the ambient temperature, or (more practically) by making its thermal time constant longer than the duration of the measurement procedure, or both. Ideally the time constant is much longer, e.g., ten times or more longer, than the measurement interval. Thus the time constant for a typical twenty-second measurement interval should be at least three or four minutes.

It is to be understood that all of the foregoing detailed descriptions are by way of example only, and not to be taken as limiting the scope of my invention—which is expressed only in the appended claims.

I claim:

1. An apparatus for estimating the flow rate of blood in a bloodstream comprising:
   means for injecting into such bloodstream a quantity of fluid whose temperature is distinctly different from that of the blood;
   means, having a reference thermocouple, for measuring changes in the temperature of the blood at a point downstream from the injection point; and
   a reference heat sink which is not temperature-controlled, thermally connected to the reference thermocouple of the means for measuring changes;
   the change-measuring means including:
      a sensing thermocouple disposed at the downstream point,
      a reference thermocouple disposed to substantially assume the temperature of the reference heat sink, and
      means for measuring the voltage produced by the sensing and reference thermocouples, operating as an opposed thermocouple pair, while the injected fluid passes the downstream point; and
      electronic means responsive to the measured voltage for determining the blood temperature changes sensed by the sensing thermocouple independently of the temperature of the reference thermocouple considered singly wherein said electronic means compensates for changes in the temperature of the heat sink while the injected fluid passes the downstream point.

2. The apparatus of claim 1, wherein:
the heat sink is very generally at an ambient temperature distinctly different from that of the blood.

3. The apparatus of claim 1, wherein:
the heat sink has high thermal conductivity;
whereby thermal effects at any part of the heat sink tend to be averaged over the entire heat sink.

4. The apparatus of claim 1, further comprising:
means for measuring the temperature of the fluid substantially at the injection point, the fluid-temperature measuring means including:
a second sensing thermocouple disposed substantially at the injection point,
a second reference thermocouple disposed to assume the temperature of the reference heat sink,
means for measuring the voltage produced by the second sensing and reference thermocouples, operating as a second opposed thermocouple pair, while the fluid is injected; and
second electronic means responsive to the measured voltage produced by the second opposed thermocouple pair for determining the blood temperature changes sensed by the second sensing thermocouple independently of the temperature of the second reference thermocouple considered singly.

5. The apparatus of claim 4 wherein said second electronic means is further comprising:
means for approximately integrating the measured voltage produced by the second thermocouple pair over injected volume of the fluid.

6. The apparatus of claim 1, wherein the electronic means further comprises:
means for registering an approximation to the effects of drift in heat-sink temperature upon the measured voltage before the fluid is injected;
means for extrapolating said registered approximation into the time period in which the injected fluid passes the downstream point; and
means for correcting the measured voltage to compensate for the extrapolated approximation;
said electronic means therein tending to compensate for drift in the electronic means itself, except for drift in the registering means and in the extrapolating means.

7. The apparatus of claim 6, wherein:
the approximation-registering means respond to the mean rate of drift of the measured voltage before the fluid is injected;
the extrapolation means provide a compensation signal that drifts at said mean rate after the fluid is injected; and
the correction means subtract the compensation signal from the measured voltage.

8. A method for use in estimating the flow rate of blood in the bloodstream from a living being's heart, comprising:
injecting into such bloodstream, at a particular point near such heart, a quantity of fluid whose temperature is distinctly different from that of the blood;
while the injected fluid passes the downstream point, measuring changes in the voltage output of an opposed thermocouple pair whose sensing junction is disposed downstream from the injection point and whose reference junction is disposed to substantially assume the temperature of a reference heat sink which is not temperature-controlled;
said measuring step being independent of the temperature of the reference heat sink considered singly; and
compensating for changes in the temperature of the heat sink while the injected fluid passes the downstream point.

9. The method of claim 8, wherein: the heat sink is very generally at an ambient temperature distinctly different from that of the blood.

10. The method of claim 8, wherein:
the heat sink has high thermal conductivity;
whereby thermal effects at any part of the heat sink tend to be averaged over the entire heat sink.

11. The method of claim 8, further comprising:
while the injected fluid passes the downstream point, also measuring the voltage output of a second opposed thermocouple pair whose sensing junction is disposed substantially at the injection point and whose reference junction is disposed to substantially assume the temperature of a reference heat sink;
said second-pair measuring step being independent of the temperature of the reference heat sink considered singly.

12. The method of claim 11, further comprising:
approximately integrating the measured voltage produced by the second thermocouple pair over injected volume of the fluid.

13. The method of claim 8, wherein the compensating step includes:
registering an approximation to the effects of drift in heat-sink temperature upon the measured voltage before the fluid is injected;
extrapolating said registered approximation into the time period in which the injected fluid passes the downstream point; and
correcting the measured voltage to compensate for the extrapolated approximation.

14. The method of claim 13, wherein:
the approximation-registering step registers the mean rate of drift of the measured voltage before the fluid is injected;
the extrapolation step provides a compensation signal that drifts at said mean rate after the fluid is injected; and
the correction step subtracts the compensation signal from the measured voltage.

* * * * *